United States Patent [19]

Weikl et al.

[11] Patent Number: 4,573,966
[45] Date of Patent: Mar. 4, 1986

[54] METHOD AND APPARATUS FOR REMOVING AND/OR ENLARGING CONSTRICTED AREAS IN VESSELS CONDUCTING BODY FLUIDS

[75] Inventors: Andreas Weikl; Volkmar Merkel, both of Erlangen, Fed. Rep. of Germany

[73] Assignee: Schneider Medintag AG, Fed. Rep. of Germany

[21] Appl. No.: 444,464

[22] Filed: Nov. 24, 1982

[30] Foreign Application Priority Data

Nov. 24, 1981 [DE] Fed. Rep. of Germany ....... 3146459
Sep. 29, 1982 [DE] Fed. Rep. of Germany ....... 3235974

[51] Int. Cl.[4] ............................................. A61M 25/00
[52] U.S. Cl. ...................................... 604/53; 604/101; 128/348.1
[58] Field of Search ...................... 128/325, 344, 348.1, 128/328; 604/49–54, 28, 43–45, 96–103, 266, 265, 269

[56] References Cited

U.S. PATENT DOCUMENTS

| 550,238 | 11/1895 | Allen | 604/101 |
|---|---|---|---|
| 2,210,744 | 8/1940 | Winder | 604/101 X |
| 2,642,874 | 6/1953 | Keeling | 604/101 |
| 2,813,531 | 11/1957 | Lee | 604/103 |
| 2,936,760 | 5/1960 | Gants | 604/101 |
| 3,316,910 | 5/1967 | Davis | 128/328 |
| 3,923,065 | 12/1975 | Nozick et al. | 128/348.1 |
| 4,091,816 | 5/1978 | Elam | 604/101 X |
| 4,224,929 | 9/1980 | Furihata | 128/5 |
| 4,295,464 | 10/1981 | Shihata | 128/328 X |
| 4,423,725 | 1/1984 | Baran et al. | 604/101 |
| 4,430,083 | 2/1984 | Ganz et al. | 604/265 X |
| 4,445,892 | 5/1984 | Hussein et al. | 604/101 |

FOREIGN PATENT DOCUMENTS

| 1069823 | 11/1959 | Fed. Rep. of Germany | 128/344 |
|---|---|---|---|
| 1460776 | 10/1966 | France | 128/328 |
| 627828 | 10/1978 | U.S.S.R. | 604/101 |
| 683756 | 9/1979 | U.S.S.R. | 604/101 |

OTHER PUBLICATIONS

Dotter et al, "Selective Clot Lysis with Low-Dose Streptokinase", Radiology, 111:31–37, Apr. 74.

Primary Examiner—Dalton L. Truluck
Attorney, Agent, or Firm—Craig and Burns

[57] ABSTRACT

An apparatus and method for comminuting and/or eliminating constricted areas in vessels of all types whereby fissures and cracks in the vessel walls during the treatment of stenosis in blood vessels and also coronary obstruction are to be avoided. A treatment catheter is used which is equipped with two inflatable balloons which seal off a constriction place in a vessel on both sides thereof whereby the degree of expansion of both balloons is externally regulatable. An inlet member for the supply of means dissolving the material of the constriction area or comminuting the same into smaller particles and an outlet member for the removal of the dissolved or comminuted material of the constriction place are provided in the walls of the treatment catheter within the area delimited by the two balloons. These inlet and outlet members are in communication with a channel accessible from the outside.

40 Claims, 11 Drawing Figures

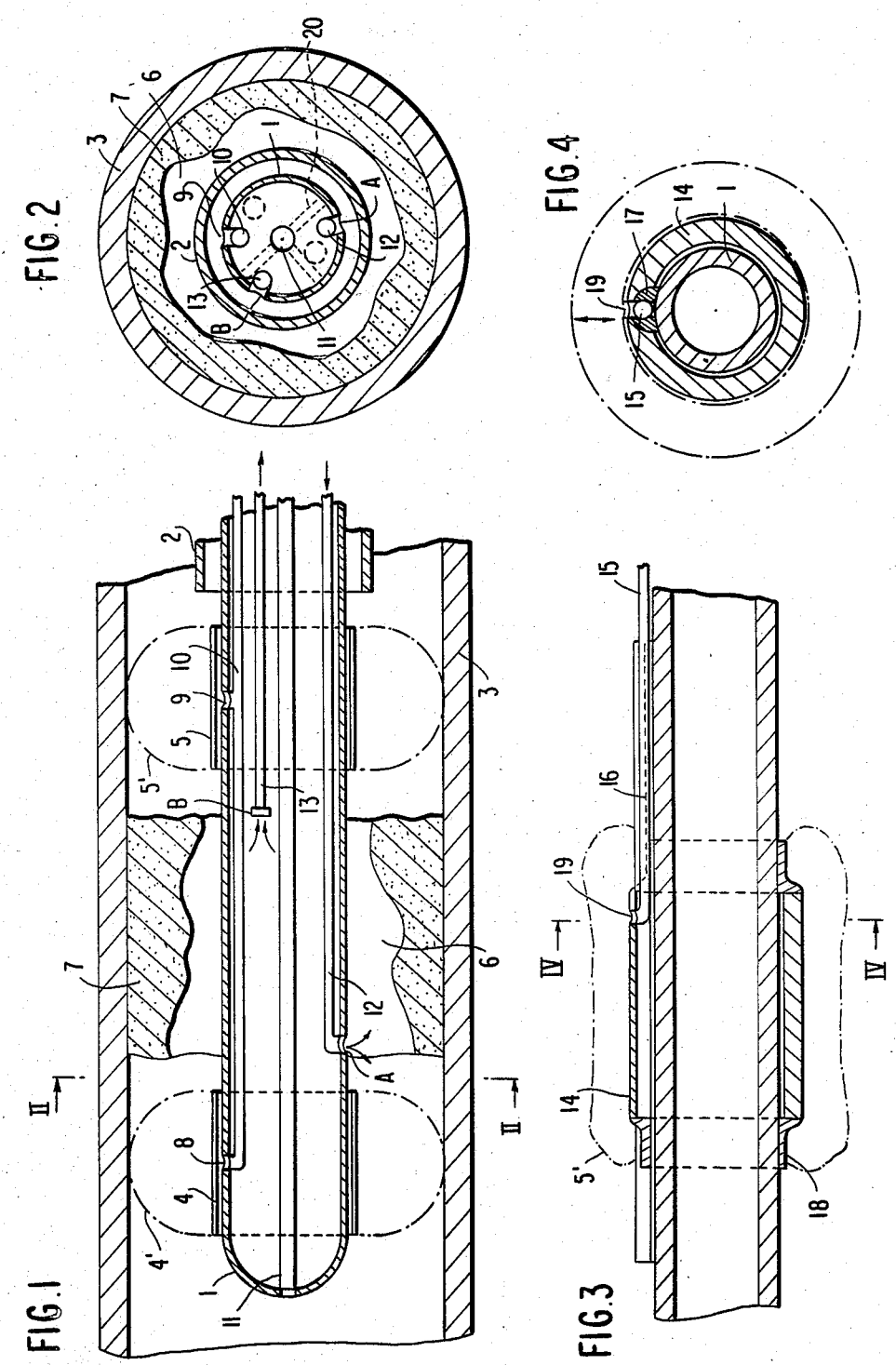

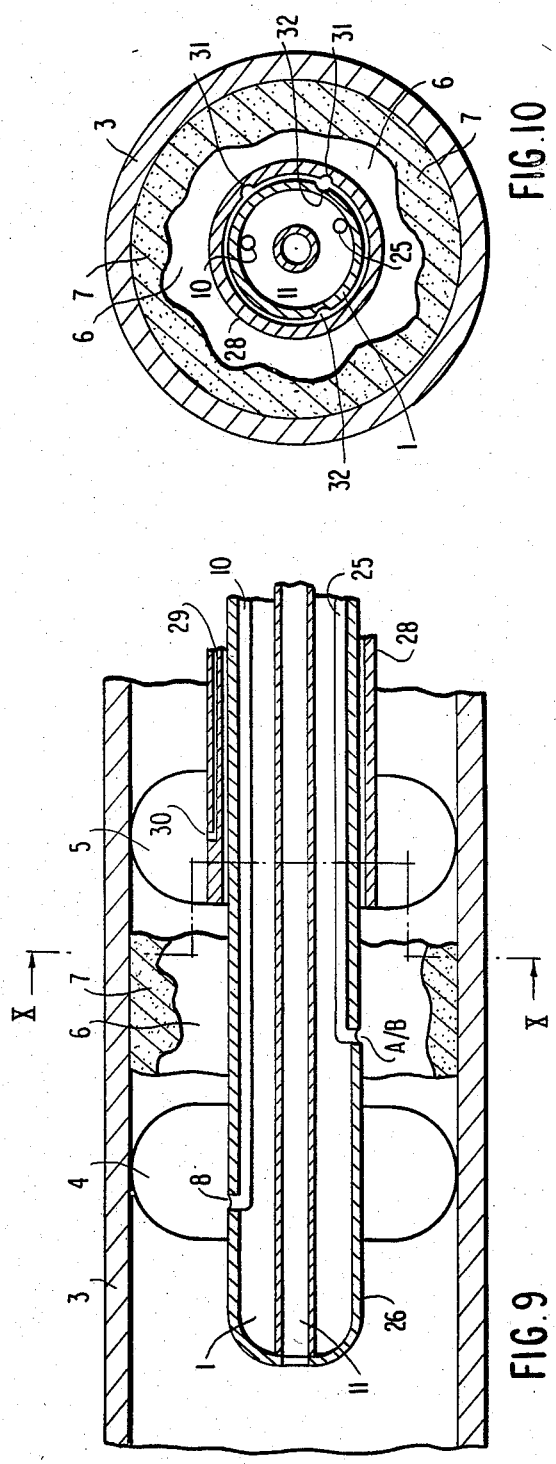
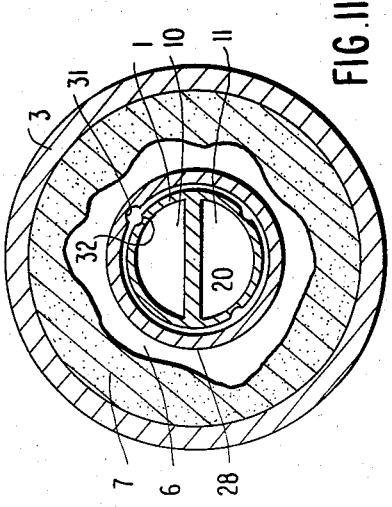
FIG. 10
FIG. 11
FIG. 9

4,573,966

METHOD AND APPARATUS FOR REMOVING AND/OR ENLARGING CONSTRICTED AREAS IN VESSELS CONDUCTING BODY FLUIDS

TECHNICAL FIELD

The present invention relates to a method and apparatus for removing and/or enlarging constricted areas (stenoses) in vessels conducting body fluids.

BACKGROUND ART

German Auslegeschrift No. 1,069,823, discloses an apparatus relating to at least two expandable balloons provided at a distance from one another at the end on the vessel side of a treatment catheter. Each balloon is connected with a channel or duct accessible from the outside and can be inflated individually by external pressure. After the insertion of the treatment catheter into a urethra, the latter can be expanded or stretched by the inflation of the balloon. A stone forming a constricted place respectively closing the urethra, is adapted to be enclosed between the balloons. In the expanded condition of the balloons, the treatment catheter is pulled out of the urethra and the stone is removed thereby. However, this may lead to complications if the stone gets jammed in between a balloon and the inner wall of the urethra, for example, when being pulled out. The stone then has to be seized anew correctly within the area delimited by the balloons by a change of the expansion of the balloons. When pulling out the catheter, the entire urethra is thereby subjected to a strong stretching, starting from the constricted place and in particular the inner wall is stressed by strong friction pressures. This may lead to cracks or detachments at least of the inner wall of the urethra.

Furthermore, German Offenlegungsschrift No. 3,028,089 discloses use of a treatment catheter for the enlargement of constricted places in the arterial system at the end of which is attached a balloon adapted to expand its circumference to a certain dimension. This balloon is placed in the area of the constriction and is filled with a liquid by way of a catheter so that the tissue causing the constriction is pressed into the wall of the blood vessel and remains there. Frequently during the dilatation, cracks in the intima of the innermost wall of the vessel system cannot be avoided. Furthermore, the danger exists that the inner vessel layers become detached in part and obstruct the free interior space of the blood vessel, as a result of which thrombi and ischemia of the organs could result in the vessel system which are supplied by the respective blood vessel. Thus, for example, a coronary obstruction may result at the coronary arteries as a result of inadequate blood supply.

SUMMARY OF THE INVENTION

The object underlying the present invention resides in the creation of an apparatus, simple in construction, economically producible and reliable in operation, with the aid of which the constrictions of any vessels conducting body fluids can be so reduced and eliminated independently of their spacial arrangement or extent in the vessel system that it will not lead to fissures or cracks in the vessel wall. With the application of the apparatus according to the present invention in blood vessels, the supply of the organ or organs located downstream of the constricted area is also to be assured during a treatment of the constricted area which lasts for longer periods of time and therewith the danger of a coronary obstruction can also be excluded in those cases.

The underlying problems are solved according to the present invention in that within the area delimited by the two balloons at least one opening is provided in the wall of the treatment catheter which forms respectively from the orifice of at least one inflow or discharge channel accessible from the outside in such a manner that means can be supplied from the outside through this or these inflow or discharge channels into the limited area, especially a material dissolving the constriction material, comminuting the same into small particles or softening the same, or a substance, especially dissolved or comminuted constricted area material, can be conducted toward the outside of the limited area through respectively these supply or discharge channels.

By the arrangement of an opening between the two balloons and the connection thereof to a channel accessible from the outside, each constricted location can be eliminated in a protected manner within a relatively short period of time by an intentional dissolution or comminution of material of the constricted areas and by one or several subsequent flushing operations of the constricted location. Substantially no disadvantageous side effect occurs thereby as a result of vessel stretching or expansion because the same is undertaken only within the healthy area of the vessel and more particularly only at two narrow locations thereof. The apparatus according to the present invention can therefore be applied in all those cases in which the constricted location is formed by substances which are adapted to be dissolved or comminuted.

By softening the material at the constricted location, its removal from the constricted location becomes particularly nonproblematical because the danger of damaging the vessel walls are completely eliminated in this case by reason of the consistency of the material of the constricted location.

According to an advantageous construction of the present invention, a supply channel may additionally be provided. At the same time, a sufficient supply of fluid through the supply channel to the organ located downstream thereof is assured during the treatment of the constricted area. It is particularly advantageous that treatment liquids, possibly also in stronger concentrated form, can be made effective over periods of time adapted to be selected at will on the material of the constricted area by means of the invention within predetermined areas of vessels conducting body fluids within an area that can be delimited.

These and other objects, features and advantages of the present invention will become more apparent from the following description when taken in connection with the accompanying drawings which show, for purposes of illustration only, several embodiments in accordance with the present invention.

BRIEF DESCRIPTION OF THE DRAWINGS

FIG. 1 is a portion of a longitudinal sectional view through a blood vessel with an introduced guide and treatment catheter as well as with blocking balloons arranged on both sides of the constricted area in accordance with the present invention;

FIG. 2 is a cross-sectional view taken along line II—II of FIG. 1;

FIG. 3 is a longitudinal cross-sectional view of a modified embodiment of a treatment catheter in accordance with the present invention with a balloon arranged thereon in a displaceable manner;

FIG. 4 is a cross-sectional view taken along line IV—IV of FIG. 3;

FIG. 9 is a longitudinal cross-sectional view through a vessel section with a still further modified embodiment of an inserted treatment catheter and with an area limiting catheter displaceable thereon;

FIG. 10 is a cross-sectional view taken along line X—X of FIG. 9; and

FIG. 11 is a cross-sectional view taken along line X—X of FIG. 9, however with a treatment catheter having only one longitudinal partition wall, as shown in FIG. 7 and FIG. 8.

DETAILED DESCRIPTION OF THE INVENTION

Figure 6:
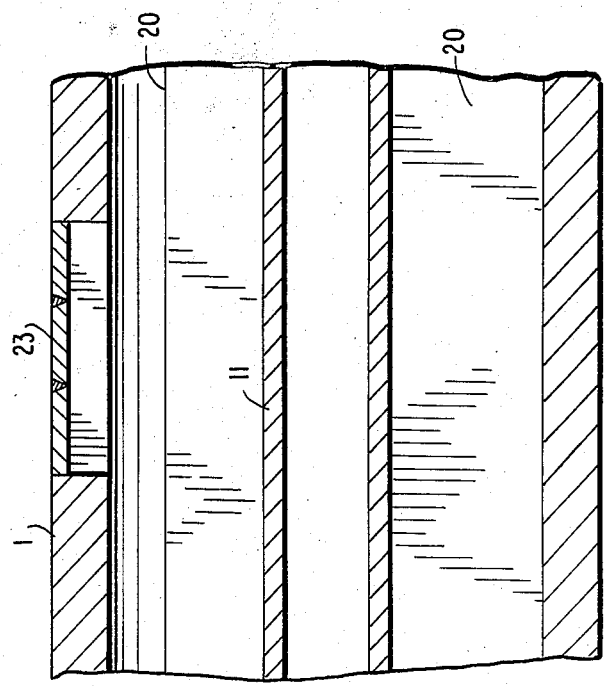
FIG. 6 is a longitudinal cross-sectional view of a treatment catheter with a partially perforated outer surface respectively intentional breakage places, taken along line VI—VI of FIG. 5.

Referring now to the drawings wherein like reference numerals are used throughout the various views to designate like parts, the treatment catheter 1 is inserted into a blood vessel 3 by a guide catheter 2. The treatment catheter 1 projects beyond the guide catheter 2 to the extent that the balloons 4 and 5 arranged on the treatment catheter 1 such that the constricted area 6 or stenosis is enclosed therebetween ahead of the end of the guide catheter 2. The stenosis 6 is customarily formed of a sponge-like calcified and fatty tissue which is indicated in the drawing by a cross-section marked with crisscrossing. In case the tissue 7 closes off the passage of the blood vessel 3 completely or nearly completely, the treatment catheter 1 or initially another instrument is forced through the same. Otherwise, the treatment catheter 1 is guided through the existing opening of the constriction 6 so that the balloon 4 in the inflated condition 4' seals off the constriction 6 on the backside thereof and the balloon 5 in the inflated condition 5' seals off the constriction 6 on the front side thereof. Thus, the blood vessel 3 is tightly sealed all around on both sides of the constricted area 6.

The expansion or inflation of the balloons 4 and 5 can take place by a gas or a liquid medium. The latter can be admitted and discharged from the outside by way of the inlet-outlet nozzles 8 and 9 and by way of a pressure duct or channel 10, whereby the quantity and pressure medium are controllable. In order that the supply of fluid of the organ or organs located downstream is assured, in particular, during longer treatment periods, during the treatment of constricted places 6 in blood vessels notwithstanding the closing off on both sides of the constricted place 6, an additional supply channel 11 is provided. It represents a type of "bypass line" to the sealed off constricted area. The supply channel 11 is preferably arranged coaxially to the treatment catheter 1. However, deviating therefrom, it may also be built in or built on in another position or in the form of a multiple channel. Blood and other fluids, may flow in by way of this supply channel 11, preferably under excess pressure from outside, with the aid of an overflow channel, out of the blood circulation, located ahead of the blockage. As a result thereof, sufficiently long operating periods are available without the danger of a coronary obstruction.

In order that only calcified and fatty tissue 7 of the constriction is attacked, but not the inner skins of the blood vessel 3, a solution of chemical substance is pumped through the inlet channel 12, having the inlet section A into the space containing the constricted area tissue 7. The chemical substance is able to dissolve the tissue 7. Digestive enzymes or similar substances are suitable examples of such chemical substances.

For other applications, such as the treatment of gall or kidney deposits or stones, other substances may be used such as dissolving acids.

Figure 8:
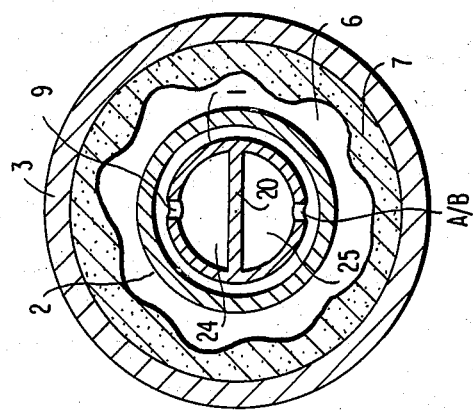
FIG. 8 is a cross-sectional view taken along line VIII—VIII of FIG. 7.
Figure 7:
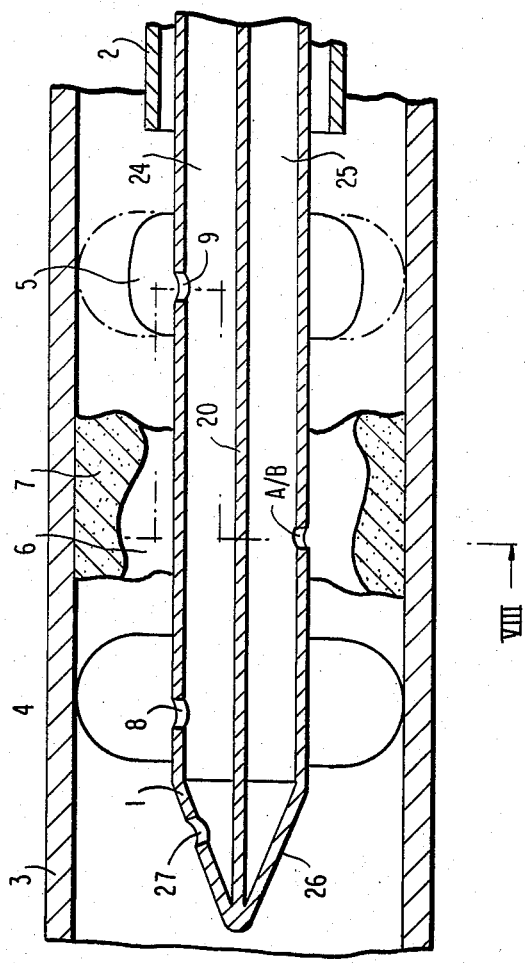
FIG. 7 is a longitudinal cross-sectional view through a vessel section with inserted treatment and guide catheter in accordance with the present invention and with a channel in the treatment catheter serving the supply and at the same time the feed of the balloon pressure.

For the removal of dissolved or comminuted particles and for softening the treatment time, a continued circulatory flushing is advantageous. This is assured by way of a return channel 13 with the outlet part B. In principal, however, it is also possible to supply the means dissolving the material 7 at the constriction or comminuting the same into smaller particles by way of a single channel and to discharge or remove the dissolved or comminuted constriction material 7 alternately by way of the same channel. FIGS. 7, 8 and 11 illustrate such a construction which will be described more fully hereinafter. Of course, the inlet channel 12 may also be used as return channel and the return channel 13 as inlet channel.

Depending on demand, the number of in and flow and return flow channels may also be increased.

In order to be able to match the size of the blockage place to the expansion of the tissue 7, it is of advantage if the balloon 5 is not arranged rigidly—as indicated in FIG. 1—but is arranged displaceably on the treatment catheter 1. Such an embodiment is illustrated in FIGS. 3 and 4. The balloon is thereby cured on a slider 14 which is movable to and fro from outside, preferably, with the aid or a more rigid synthetic fiber wire—preferably, pearl on wire 15 or the like. Synthetic fiber wire 15 may thereby be guided in a channel 16 which is accommodated in an elongated raised portion 17 of the treatment catheter 1 serving simultaneously for the guidance of the slide member 14, that is, practically in its wall reinforcement. At the same time, the inflation medium may be supplied and discharged through this channel 16 and the pressure thereof can be regulated from the outside.

In order that the gap between the slide member 14 and the outer wall of the treatment catheter 1 is sealed off completely satisfactorily, a sealing sleeve 18 is provided at least at the side facing the constriction 6, which by a particular configuration of the balloon 5 additionally contributes to the effective seal at this sealing place. Reference numeral 19 designates the nozzle. Gaseous or liquid medium for the expansion of the displaceable balloon 5 is supplied and discharged through the nozzle.

Figure 5:
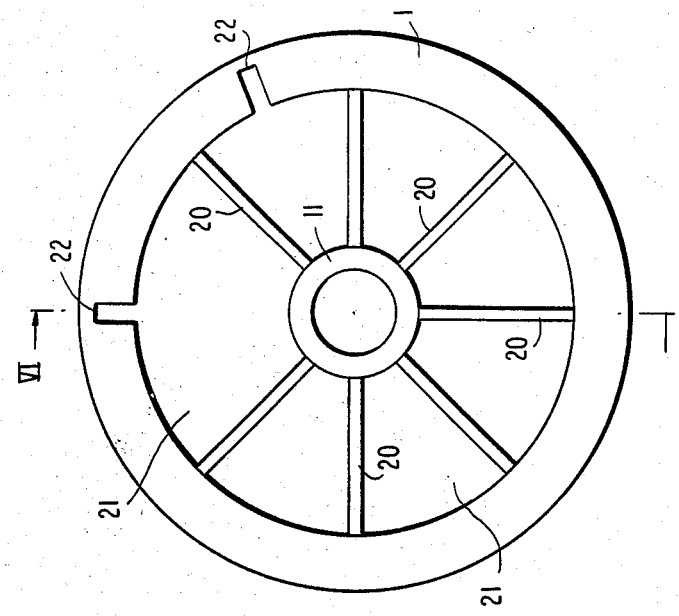
FIG. 5 is an elevational view of a still further modified embodiment of a treatment catheter with partition walls for the formation of channels or ducts for the supply and discharge of liquids or gases in accordance with the present invention.

In lieu of the hose-shaped channels 10, 12 and 13 fed and secured at the wall parts of the treatment catheter 1, the interior space of the treatment catheter 1 can also be subdivided correspondingly by longitudinal partition walls 20 (FIG. 2 and FIG. 5) so that chambers 21 result through which, depending on need, the corresponding medium can be conducted.

Furthermore, it is advantageous in some cases—especially with the application of longitudinal partition walls 20—to provide the walls of the treatment catheter 1 with perforations 23 in lieu of the provision of inlet—outlet nozzles 8 and 9 respectively of the nozzles A and B at the ends of the channels 12 and 13. At these locations, whereby these perforations, as can be seen from FIG. 5 and FIG. 6, will result only after the breaking open of intentional breakage places 22 so that the length of the perforated catheter part can be adjusted only prior to the interaction corresponding to the size of the constriction to be treated.

FIG. 7 and FIG. 8 illustrate a further embodiment according to the present invention with the single longitudinal partition wall 20. Thus, the treatment catheter 1 is subdivided into two channels. One channel is constructed as combined pressure and supply channel 24. The other channel is constructed as a combined inlet and discharge channel 25 for the constriction 6. Channel 24 includes within the area of each balloon 4 and 5 openings 8 and 9 and at the end of the treatment catheter 1 on the side of the vessel, a discharge opening 27. The other channel includes within the delimited area an inletoutlet opening A/B. Because of its possible smaller diameter, this treatment catheter is particularly suited for small vessel cross-sections. On one hand, it is achieved as a result of a liquid pressure produced in the channel 24 by means of a liquid externally supplied, especially of a supply liquid for organs located downstream, for example, blood can be supplied at the same time the balloons 4 and 5 can be expanded. As a result thereof, the isolated area about the constriction 6 can be sealed off on both sides. The liquid then leaves under pressure through the discharge opening 27. On the other hand, the substance dissolving the material of the constriction can be pumped into the constriction 6 through the channel 25 either continuously or intermittently and subsequently dissolved material of the constriction area can be withdrawn together with the remaining substance. As a result thereof, the aimed at effect becomes possible together with a treatment catheter 1 which can be manufactured in a simple manner, whereby the cross-section thereof can be kept very small.

According to a further advantageous construction of the present invention, one or the other of balloons 4 or 5 may be of a construction which has a more elastic casing or wall than the other. In the embodiment according to FIG. 7 and FIG. 8, this is the balloon 4. It is possible thereby to so adjust and regulate the pressure that both balloons 4 and 5 seal off and, for example, during the withdrawal of the substances out of the delimited area the balloon 4 still seals off whereas the balloon 5 no longer forms an effective seal as shown in FIG. 7. It becomes possible thereby to also utilize the guide catheter 2 for flushing or suction because with such a pressure adjustment the constriction 6 is also accessible from the side of the guide catheter 2.

Appropriately, the ballons 4 and 5 of the apparatus according to the present invention may be so constructed that they assume a predetermined shape and size and then no longer grow in size even with the application of a considerably higher pressure.

In the advantageous embodiments of the present invention illustrated in FIGS. 9, 10 and 11, the balloon 5 which is located further removed from the end 26 on the side of the vessel of the treatment catheter 1, is provided on the end of an area limiting catheter 28 which is slidably arranged on the treatment catheter 1. The area limiting catheter 28 is provided with a pressure channel 29 which is preferably integrated into the wall of the area limiting catheter 28 and which terminates in an opening 30 provided inside of the balloon 5. By a displacement of the area limiting catheter 28 the length of the limited area can be selected corresponding to the requirements and can be sealed off or opened again by the separate expansion possibility of the balloon 5. Also in this case, a space may be advantageously left between the treatment catheter 1 and the area limiting catheter 28 and this space can be used for purposes of flushing or suction. For purposes of a very compact type construction, one or several notches 31 may also be provided for that purpose at the inner wall of the area limiting catheter 28 and/or notches 32 at the outer wall of the treatment catheter 1, as illustrated in FIG. 10 and FIG. 11. In order to achieve thereby larger cross-sections for throughflow, the notches 31 of the limiting area catheter 28 may thereby be arranged opposite the notches 32 of the treatment catheter 1. Also with this constructive solution according to the present invention a single longitudinal partition wall 20 may be provided in the treatment catheter 1—as shown in FIG. 11—and the treatment catheter 1 may be provided with an opening as described by reference to FIG. 7 so that the effects described in connection therewith are also attainable. The apparatus according to FIGS. 9, 10 and 11 may further include a guide catheter 2 (not shown).

A catheter according to the present invention for the treatment of constricted locations can be used with all types of vessels conducting body fluids, that is, with all types of blood vessels or other vessels conducting other liquids, such as cerebral spinal channels or also with larger lymph ducts.

Further fields of application—in addition to the main application areas of the treatment of constrictions in blood vessels—are for example the treatment of constrictions in the bile duct, in the pancreas duct or in the cerebral spinal duct.

It is also possible with the present invention to bring chemical substances in high or even more highly concentrated form to the vessel areas with the aim to initiate from these vessel areas capillary vesicles starting revascularization. In particular, the materials, namely angiotropine which are isolated out of white blood corpulscles may be considered for stimulating revascularization. The dissolving material can be an enzyme, preferably a digestive enzyme, acid or alkaline. Nitric acid and sodium hydroxide can be used as the dissolving material. The reaction time for the dissolving material on the constricted area can be limited by inhibiters, such as enzyme blockers, neutralizing acids or lyes to a predetermined time duration. Thus, the constricted area material can be dissolved, softened or comminuted into smaller particles prior to circulatory flushing to remove the material. The constricted area material can be removed as a whole after softening upon the withdrawal of the treatment catheter. The latter can occur with reduced pressure of one or both balloons.

The constriction treatment with the catheter according to the present invention may be undertaken in several stages, possibly with the use of different treatment media and/or different concentrations of the treatment media. The materials used in the fabrication of the apparatus of the present invention, namely, the catheter and its functional components, are conventional.

While we have shown and described several embodiments in accordance with the present invention, it is understood that the same is not limited thereto but is susceptible of numerous changes and modifications as known to those skilled in the art and we therefore do not wish to be limited to the details shown and described herein but intend to cover all such changes and modifications as are encompassed by the scope of the appended claims.

We claim:

1. An apparatus, adapted for use with means for supplying a dissolving fluid to an isolated area in a vascular passageway, of a size to fit within a vascular passageway conducting body fluids, such as arteries and veins conducting blood, for selectively isolating constricted areas in the vascular passageway, such as stenosis, and treating the isolated area with the dissolving fluid, the apparatus comprising a flexible treatment catheter, two balloon means disposed near the end of the flexible catheter, each of the two balloon means being expandable by a pressure medium so as to contact the inside of the passageway and being controllable from outside the catheter, the two balloon means being disposed one after the other at such a distance that one balloon means is adapted to be placed ahead of and the other behind the constricted area, the two balloon means being expandable for operatively sealing off and thereby isolating the constricted area, at least two partition walls extending substantially the full length of the catheter subdividing the catheter into at least four channel means, opening means in said catheter connecting two of the at least four channel means to the area isolated by the two balloon means, whereby dissolving fluid for treatment of the isolated area can be supplied to the isolated area through one of the opening means from outside the catheter and removed from the isolated area through another of said opening means.

2. The apparatus according to claim 1, wherein the dissolving fluid includes a material operable to selectively dissolve, comminute and soften material causing the stenosis in the in the constricted area.

3. The apparatus according to claim 1, wherein the at least four channel means include an additional supply channel means which, on the one hand, terminates in the passageway at the end of the treatment catheter downstream of the two balloon means and, on the other, is accessible from one of the outside and within the passageway ahead of the isolated area whereby, during treatment, substances can be conveyed through the isolated area.

4. The apparatus according to claim 1, wherein each of the two balloon means is connected with at least one externally accessible channel means so that the degree of expansion of each of the two balloon means is independently regulatable.

5. The apparatus according to claim 1, wherein the two balloon means are connected with a common pressure channel means.

6. The apparatus according to claim 5, wherein the common pressure channel means is at the same time the supply channel means.

7. The apparatus according to claim 1, wherein the two balloon means have different elasticities whereby with increasing pressure first one and then the other balloon means reach maximum expansion and with decreasing pressure one of the balloon means is still at maximum expansion while the other balloon means is at less than maximum expansion and no longer contacts the inside of the passageway.

8. The apparatus according to claim 7, wherein the two balloon means are constructed so that they are able to carry out only a limited expansion sufficient for closing off the constricted area.

9. The apparatus according to claim 1, wherein the at least two of the at least four channel means are arranged coaxially with the treatment catheter.

10. The apparatus according to claim 1, wherein all of at least four channel means are formed by the at least two partition walls provided in the treatment catheter.

11. The apparatus according to claim 1, wherein the opening means comprises perforations in the treatment catheter.

12. The apparatus according to claim 11, wherein digestive enzymes or similarly effective substances are adapted to be supplied as dissolving or flushing agents for the dissolution or elimination of tissue forming a constriction in the constricted area.

13. The apparatus according to claim 1, wherein the balloon means closing off the constricted area on the inlet side thereof is displaceably arranged on the outer wall of the treatment catheter.

14. The apparatus according to claim 13, wherein a slide means serves as displacement member for the movable balloon means which is adapted to be moved to and fro from the outside.

15. The apparatus according to claim 14, wherein the slide means is guided on the surface of the treatment catheter.

16. The apparatus according to claim 14, wherein the slide means serves as carrier of a hose for the further conduction of the pressure medium for the balloon means connected therewith.

17. The apparatus according to claim 16, wherein the slide means is constructed as carrier of the hose for the further conduction of the pressure medium for the balloon means connected therewith.

18. The apparatus according to claim 14, wherein the slide means includes a sealing sleeve at least on the side facing the constricted area, said sealing sleeve being securely pressed by a pressure medium onto the outer surface of the treatment catheter.

19. The apparatus according to claim 18, wherein the sealing sleeve is pressed onto the outer surface of the treatment catheter by the inflated balloon means.

20. The apparatus according to claim 14, wherein the slide means is constructed as an area limiting catheter surrounding a treatment catheter.

21. The apparatus according to claim 20, wherein a channel means leading toward the outside is integrated into the area limiting catheter.

22. The apparatus according to claim 20, wherein at least one of inflow and discharge channel means is formed by at least one notch means in one of the inner and outer walls of the area limiting catheter and of the treatment catheter respectively.

23. The apparatus according to claim 22, wherein the notch means of the treatment catheter are provided opposite the notch means of the area limiting catheter.

24. The apparatus according to claim 23, wherein the treatment catheter is subdivided by a longitudinal partition wall into a pressure channel for one balloon means and into a supply channel, and in that the notch means serve as at least one of inflow and discharge channel means for the limited area.

25. A method for selectively removing and enlarging constricted areas in passageways conducting body fluids, such as stenosis in arteries and veins conducting blood, the method comprising inserting a flexible treatment catheter sized to fit within a vascular passageway in a constricted area of said vascular passageway, the catheter having two balloon means disposed near the end of the flexible catheter, the two balloon means being expandable by a pressure medium so as to contact the inside of the passageway and being controllable from outside the catheter, at least two longitudinal partition walls extending substantially the full length of the catheter for subdividing the catheter into at least four channels, two of the at least four channels leading into an area adapted to be sealed off by the expanded two balloon means, and opening means connecting said two of the at least four channel means to the area sealed off by the balloon means; positioning the two balloon means so as to be disposed one after the other at such a distance that one balloon means is ahead of and the other behind the constricted area; sealing off a section of the passageway containing the constricted area by expanding the two balloon means; applying to the sealed off constricted area a dissolving material of predetermined concentration for a predetermined period; removing dissolved material of the constricted area out of the sealed off area of the passageway; and withdrawing the catheter.

26. The method according to claim 25, wherein the method includes the step of carrying off the dissolved constriction material through a supply channel of the treatment catheter.

27. The method according to claim 25, wherein the method includes the step of controlling the pressure of the two balloon means selectively individually and in common.

28. The method according to claim 27, wherein the method includes the step of controlling the pressure in the balloon means individually, wherein a different pressure is achievable in each the two balloon means so that in the balloon means ahead of the constricted area, a lower pressure is possible than in the balloon means downstream of the constricted area.

29. The method according to claim 25, wherein the method includes the step of introducing the dissolving agent in a manner such that the constricted area material is only softened so that the material can be removed as a whole by the treatment catheter during withdrawal of the treatment catheter out of the passageway.

30. The method according to claim 25, wherein the method includes the step of introducing the dissolving material so that the constricted material is comminuted into smaller particles and is conducted away through a supply channel of the treatment catheter.

31. The method according to claim 25, wherein the method includes the step of introducing dissolving material including enzymes, preferably digestive enzymes, acids or alkaline.

32. The method according to claim 31, wherein the method includes the step of introducing nitric acid as an acid dissolving material.

33. The method according to claim 31, wherein the method includes the step of introducing sodium hydroxide as an alkaline dissolving material.

34. The method according to claim 25, wherein the method includes the step of limiting the reaction time for the dissolving material on the constricted area material by inhibiters, such as enzyme blockers, neutralizing acids or lyes, to a predetermined time duration.

35. The method according to claim 25, wherein the method includes the step of circulatory flushing to remove the dissolved constriction area material, softened constriction area material or the constriction area material comminuted into smaller particles.

36. The method according to claim 35, wherein the double balloon catheter is used for realizing the flushing circulation.

37. The method according to claim 27, wherein the method includes the step of reducing the pressure of one or both of the balloon means before the withdrawal of the treatment catheter.

38. The method according to claim 25, wherein the method includes the step of removing the material of the constricted area that is softened, divided into smaller particles or dissolved through a channel of the treatment catheter to the outside from the area sealed off by the two balloons.

39. The method according to claim 25, wherein the method includes the step of maintaining the blood circulation in the treated blood passageway to the organs by way of another channel in the treatment catheter.

40. The method according to claim 25, wherein the method includes the step of maintaining the flow of body fluids conducted in the passageway.

* * * * *